United States Patent [19]

Edmundson et al.

[11] Patent Number: 5,020,629
[45] Date of Patent: Jun. 4, 1991

[54] LISTENING ENHANCEMENT DEVICE

[76] Inventors: Paul G. Edmundson, 1341 Drake Ave., Burlingame; Terry Merritt, 730 Hillsborough Blvd., Hillsborough, both of Calif. 94010

[21] Appl. No.: 448,282

[22] Filed: Dec. 11, 1989

[51] Int. Cl.$^5$ ............................................. G10K 11/28
[52] U.S. Cl. ............................................. 181/136; 181/129
[58] Field of Search ........................ 181/129, 133, 136

[56] References Cited

U.S. PATENT DOCUMENTS

| | | | |
|---|---|---|---|
| 1,820,107 | 8/1931 | Agee | 181/136 |
| 3,938,616 | 2/1976 | Brownfield | 181/136 |
| 4,574,912 | 3/1986 | Fuss et al. | 181/129 |
| 4,771,859 | 9/1988 | Breland | 181/136 |

*Primary Examiner*—Benjamin R. Fuller

[57] ABSTRACT

A listening enhancement device in which a flat body (18) with a ear-hook (14) cutout can be converted to a sound gathering acoustical scoop by engagement of a fastener system located on the body (18) of the device. Once fastened into its functional shape the device can be independently engaged wtih the ear. The device is made in mirror image pairs so one device is specifically for the left ear and the other for the right. The device is reversible as to which side of the body (18) forms the sound gathering acoustic scoop. When reversed the device that is specific to the left ear becomes specific to the right ear and visa versa. Each side of the body (18) of the device has its own acoustic properties. By reversing the device the user can choose which acoustic properties most benefit them. The device is adjustable in acoustic gain. This is accomplished by different fastener engagement positions, which in turn change the size and shape of the sound gathering acoustic scoop. The body (18) is soft and flexible, providing resistance to damage and reducing discomfort and skin irritation to the user. The body (18) has acoustic properties that preserve a natural spectral balance, being free of colorations or resonances in the audio spectrum.

5 Claims, 1 Drawing Sheet

LISTENING ENHANCEMENT DEVICE

BACKGROUND

1. Field of Invention

This invention relates generally to hearing aids and more specifically to non-electronic acoustic devices worn on the user's ear to increase hearing reception

2. Description of Prior Art

Numerous acoustical devices that gather directional sound to the ear exist in prior art. For example U.S. Pat Nos. 4,574,912; 3,938,616 and 1,820,107 all are examples of such prior art. While these devices may be useful for their intended purpose they are of more complexity than the present invention. The designs in prior art have many disadvantages. Some are; A) limited portability, due to bulky and frail design. This makes it difficult for the user to carry the device in a pocket. B) User discomfort due to the weight and rigidity of the materials needed for the engagement of these devices to the user. C) Colorations and resonances in the audio spectrum, due to the use of rigid and semi rigid components forming their acoustical scoops for capturing sound. D) Costly manufacturing, due to more parts to produce and assemble.

OBJECTS AND ADVANTAGES

A principle object of the present invention is to provide a listening enhancement device with similar acoustic benefits that cupping your hand behind your ear provides. Several objects and advantages of the present invention are;

A) To provide a listening enhancement device that consists of two independent flat bodies. These bodies convert to their functional shape by fasteners. This provides compactness for storage and portability.

B) To provide a listening enhancement device that is soft and flexible that will not cause irritation to the user. This also provides reduced chance of damage to the device while being carried in the pocket of the user.

C) To provide a listening enhancement device that independently engages with and stays on the users ears by the force of gravity eliminating the discomfort caused by head bands or other apparatus that rely on pressure to secure the device to the user's head or ears.

D) To provide a listening enhancement device that's lightweight so the user can wear the device for extended periods of time.

E) To provide a listening enhancement device that is similar in acoustic properties to the epidermal tissues of the ear, face and hand. This provides a natural spectral balance free of colorations or resonances in the audio spectrum.

F) To provide a listening enhancement device that is adjustable in acoustic gain.

G) To provide a listening enhancement device that has acoustic scoops for capturing sound that are reversible—each side having different acoustic properties.

H) To provide a listening enhancement device that is comprised of few parts to provide simplicity and ease of manufacture.

DETAIL DESCRIPTION OF DRAWINGS

Figure 1:
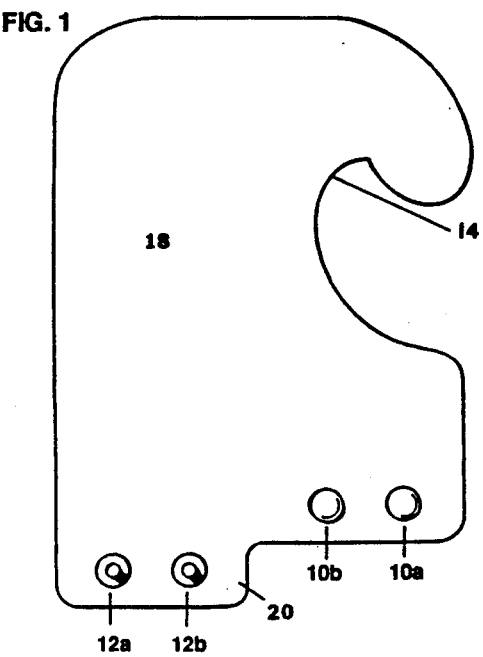
FIG. 1 View of the invention lying flat
FIG. 1A View of the invention lying flat reverse side
FIG. 2 View of the invention on the users left ear
FIG. 2A View of the invention reversed on the users right ear
FIG. 3A View of the invention with both snaps engaged
FIG. 3B View of the invention with one snap engaged (outside female, inside male)
FIG. 3C View of the invention with one snap engaged (inside female, outside male)

FIG. 1 Shows the present invention lying flat. In the preferred embodiment a leather body 18 with its smooth side up is cut to the shape illustrated in FIG. 1. An ear hook 14 cut out is located above paired female snap members 10A, 10B. Paired male snap members 12A, 12B are located on a tab 20 that is cut from and continuous with the leather body 18.

Figure 1A:
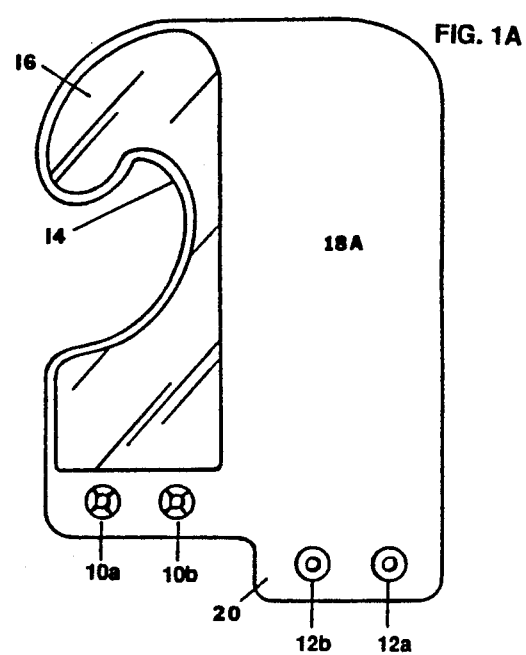

FIG. 1A. Shows the reverse side of FIG. 1. In the preferred embodiment a plastic reinforcement 16 is laminated on the suede side of the leather 18A.

Figure 2:
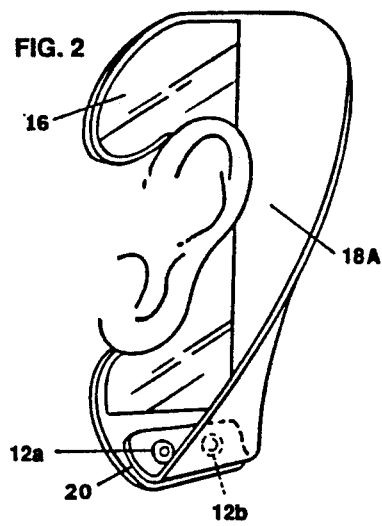

FIG. 2 Shows the present invention on user's left ear with the reinforcement 16 in view, the suede side of the leather 18R forming the inside, or sound gathering area of the acoustic scoop. The smooth side of the leather body 18 forming the outside of the acoustic scoop, Outside male snap member 10A is in view.

Figure 2A:
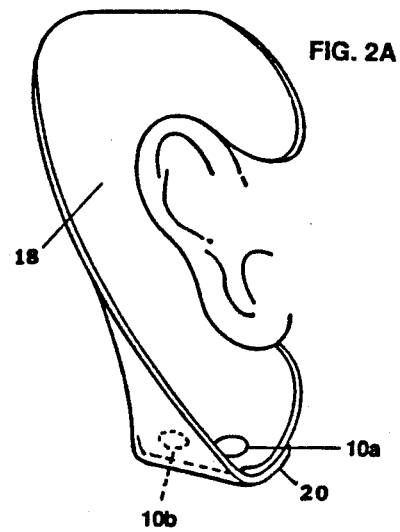

FIG. 2A Shows the present invention reversed on the users right ear. The smooth side of the leather 18 forms the inside or sound gathering area of the acoustic scoop. The suede side of the leather forms the outside of the acoustic scoop. Outside female snap member 12A is in view. Note the reinforcement 16 is hidden from view when the device is used in the reverse mode.

Figure 3A:
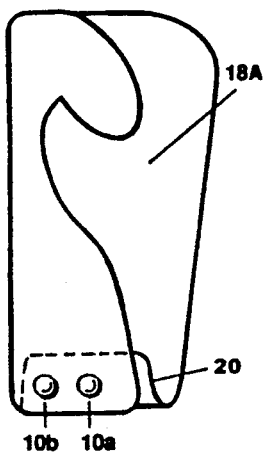

FIG. 3A Shows the present invention with both female snap members 10A, 10B engaged with the two male snap members hidden from view. The outside of the hook 14 which sits against head when the device is placed on the ear. The outside of device is the smooth leather body 18 The suede side of the leather body 18A forms the inside of acoustic scoop.

Figure 3B:
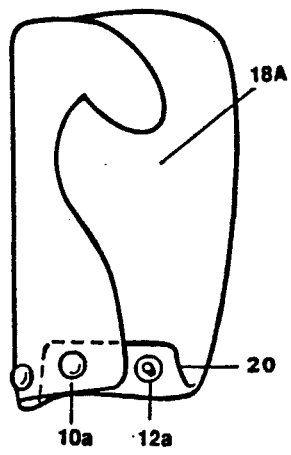

FIG. 3B Shows the present invention with only the outside female snap member 10A engaged with the inner male snap member 12B (hidden from view).

Figure 3C:
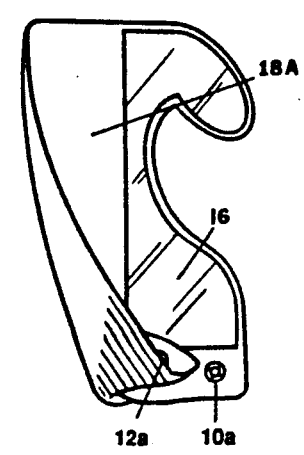

FIG. 3C Shows the present invention with only the inside female snap member 10B engaged with the outside male snap member 12A (hidden from view).

From the description above the advantages of our listening enhancement device become evident:

A) A Flat flexible body that converts to its functional shape by snap type fasteners. Eliminating the bulk of molded and ridged devices in prior art. This provides many advantages in packaging, shipping, storage, portability and damage resistance.

B) A flat flexible body that each side has its own acoustic properties. Reversibility allows the sound capturing area of the acoustic scoop can be formed with either side of the embodiment, providing a device with simplicity and variable spectral balance not available in devices in prior art C) An acoustic scoop thats size and shape is adjustable by varying snap engagement positions. Providing adjustable acoustic gain with simplicity not available in devices in prior art.

D) The preferred embodiment consists of few component parts: A leather body, plastic reinforcement and two snap sets. Providing economical manufacture, yielding a very adaptable listening enhancement device.

OPERATION DESCRIPTION OF THE PREFERRED EMBODIMENTS

The flat leather body 18 has a tab 20 cutout. Located on the tab 20 are a pair of male snap members 10A, 10B The Tab 20 gets folded upwardly so the male snap members 10A, 10B are at the same level as female snap members 12A, 12B . There after, the male snap members 10A, 10B are folded over to engage with the female snap members 12A, 12B With the snap sets engaged the flat leather body 18 is converted into a listening enhancement device. The device is now ready for engagement with the users ear. Specifically the top of the ear hook 14 engages with the top of the ear. The remainder of the ear hook 14 rests against the back of the ear.

The flat leather piece 18 has a reinforcement 16 laminated to it. The reinforcement 16 is laminated to the area surrounding the ear hook 14 . The reinforcement 16 gives the flat leather piece 18 the structural support and rigidity necessary to form the acoustic scoop when one or both snap sets are engaged. The reinforcement 16 is also necessary for stability and comfort when the device is engaged with the ear.

The present invention is reversible. This is accomplished by first folding the body 18 so the male snap members 12A, 12B are directly below the female snap members 10A, 10B . Secondly the tab 20 is folded upward so as to engage to male snap members 12A, 12B with the female snap members 10A, 10B. Each side of the body 18 has its own acoustic properties. The leather smooth finished side has more acoustic gain in the mid - high frequencies of the audio range than the leather's suede side which is spectrally neutral. People with mid - high frequency hearing loss may benefit from emphases in this frequency range. Most people will experience improved listening clarity resulting from a mid -high frequency emphases. Audiophiles desire spectral neutrality for critical music listening. The reversibility of the invention provides a great benefit for the user giving them the choice of spectral balance that works best for them.

The present invention has three different gain positions on each side of the device giving the user a total of six different acoustic tunings. The first gain position is accomplished by engaging male snap member 12A with female snap member 10B. The sound gathering acoustic scoop becomes less cup-like producing less gain than the other snap positions. This gain position works well for listening to recorded music on a home audio system, Improving the focus of the stereo image and increasing the dynamic contrast.

The second gain position is accomplished by engaging both male snap members 12A, 12B with both female snap members 10A, 10B. The sound gathering acoustic scoop becomes more cup-like than the previously described gain position and produces more gain., This gain position works well for use at concert halls and theaters.

The third gain position is accomplished by engaging male snap member 12B with female snap ,member 10A. In this position the sound gathering acoustic scoop becomes most cup-like producing more gain than either previously described gain positions. This gain position works well for users with slight hearing loss. This snap position is also beneficial in other uses where maximum gain and directionality is desirable, such as lectures and listening to birds and other animals in nature.

The present inventions changeable acoustic gain feature make the device very adaptable to the user's needs. The present inventions body 18 has very specific properties. The body must be made from a material with memory so when one or both snap sets are engaged the body tries to spring back to its original disposition.

While the body 18 must have memory. It must be soft and flexible. This provides damage resistance and reduced skin irritation to the user, minimizing discomfort.

The body 18 should have similar acoustic properties to the epidermal tissues of the ear, face, or hand to preserve a natural spectral balance and to be free of colorations or resonances in the audio spectrum.

The body 18 should be made from a material that has different acoustic absorption, reflection and diffusion properties on each side of the material. In the present inventions preferred embodiment leather in 2 ½ to 3 ½ oz. weight meets all of the specific properties discussed above.

The description of the present invention outlined above contains many specificities. These should not be construed as limitations on the scope of the invention but rather as an exemplification of one preferred embodiment there of. Many other variations are possible. For example, the body can have other shapes, so when the body is converted to its functional shape the sound gathering acoustic scoop can be larger or smaller with greater or lesser cup-like shape. The fastener system can be a sliding and locking channel or hook and loop fabric like fastener. The body of the device could by made out of various materials, including rubber, plastic, cloth, paper, or composites of laminates there of. The invention could be manufactured by injection molding rendering an entire embodiment from a single component with out departing from the spirit of the invention. Thus the scope of the invention should be determined by the appended claims and their legal equivalents.

We claim:

1. A convertible listening enhancement device adapted to be attached to a peripheral portion of an outer ear of a user, comprising:

a flat flexible body having a first surface composed of one material and a second surface composed of another material, an elongated flange portion, and a cut-out area of predetermined configuration provided in a peripheral side edge portion of said body, said cut-out area defining a hook structure for attachment to said peripheral portion of said outer ear of said user, said hook structure being reinforced to provide a higher rigidity than other portions of said flat body by attaching a reinforcing member shaped according to the configuration of said cut-out area defining said hook structure;

said flat body of flexible materials being bendable to form an adjustable scoop structure that extends away from and surrounds an outer portion of the outer ear when said hook structure is attached to the peripheral portion of the outer ear, said scoop structure defining a sound gathering means for sound energy directed into said scoop structure; and fastening means provided on said flange portion and a portion below said hook structure for selective engagement in securing and maintaining said flat body in the form of said scoop structure.

2. The convertible listening enhancement device of claim 1, where said scoop structure for gathering sound includes said first surface of said one material.

3. The convertible listening enhancement device of claim 1, wherein said scoop structure for gathering sound includes said second surface of said another material.

4. The convertible listening enhancement device of claim 1, wherein said first surface of said one material has acoustic characteristics different from said second surface of said another material.

5. The convertible listening enhancement device of claim 1, wherein said fastening means include at least a set of male fasteners on said flange portion and a set of female fasteners on said portion below said hook structure, whereby said flange portion is bendable in a position for connecting said male and female fasteners upon the formation of said scoop structure while also allowing for said scoop structure to be varied in shape to adjust acoustical gain by selecting which of the male and female fasteners are to be connected.

* * * * *